(12) United States Patent
Freiman et al.

(10) Patent No.: US 11,207,043 B2
(45) Date of Patent: Dec. 28, 2021

(54) MYOCARDIAL CT PERFUSION IMAGE SYNTHESIS

(71) Applicant: KONINKLIJKE PHILIPS N.V., Eindhoven (NL)

(72) Inventors: Mordechay Pinchas Freiman, Zichron-Yaakov (IL); Liran Goshen, Pardeds-Hanna (IL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 54 days.

(21) Appl. No.: 16/497,026

(22) PCT Filed: Mar. 20, 2018

(86) PCT No.: PCT/EP2018/057025
§ 371 (c)(1),
(2) Date: Sep. 24, 2019

(87) PCT Pub. No.: WO2018/172359
PCT Pub. Date: Sep. 27, 2018

(65) Prior Publication Data
US 2020/0375564 A1    Dec. 3, 2020

(30) Foreign Application Priority Data
Mar. 24, 2017 (EP) ..................................... 17162716

(51) Int. Cl.
*A61B 6/00* (2006.01)
*G16H 30/40* (2018.01)
(Continued)

(52) U.S. Cl.
CPC .............. *A61B 6/507* (2013.01); *A61B 6/466* (2013.01); *A61B 6/504* (2013.01); *A61B 6/5205* (2013.01);
(Continued)

(58) Field of Classification Search
CPC ... G06T 7/0012; G06T 7/0014; G06T 7/0016; G06T 7/50; G06T 7/55; G06T 7/579;
(Continued)

(56) References Cited

U.S. PATENT DOCUMENTS 8,548,778 B1    10/2013  Hart
9,078,564 B2 *   7/2015  Taylor ..................... G06T 15/10
(Continued)

FOREIGN PATENT DOCUMENTS

WO    WO2010020933 A2    2/2010
WO    WO2014091339 A1    6/2014
(Continued)

OTHER PUBLICATIONS

PCT International Search Report, International application No. PCT/EP2018/057025, dated Jul. 3, 2018.
(Continued)

*Primary Examiner* — Anastasia Midkiff
(74) *Attorney, Agent, or Firm* — Larry Liberchuk

(57) ABSTRACT

The present invention relates to image processing devices and related methods. The image processing device (10) comprises a data input (11) for receiving spectral computed tomography volumetric image data organized in voxels. The image data comprises a contrast-enhanced volumetric image of a cardiac region in a subject's body and a baseline volumetric image of that cardiac region, e.g. a virtual non-contrast image, wherein the contrast-enhanced volumetric image conveys anatomical information regarding coronary artery anatomy of the subject. The device comprises a flow simulator (12) for generating, or receiving as input, a three-dimensional coronary tree model based on the volumetric image data and for simulating a coronary flow based on the three-dimensional coronary tree model. The device comprises a perfusion synthesis unit (13) for gener- (Continued)

ating a perfusion image representative of a blood distribution in tissue at at least one instant in time taking at least the baseline volumetric image and said coronary flow simulation into account.

15 Claims, 2 Drawing Sheets

(51) Int. Cl.
*G06T 7/00* (2017.01)
*G06T 7/55* (2017.01)

(52) U.S. Cl.
CPC .......... *G06T 7/0012* (2013.01); *G06T 7/0014* (2013.01); *G06T 7/0016* (2013.01); *G06T 7/55* (2017.01); *G06T 7/97* (2017.01); *G16H 30/40* (2018.01)

(58) Field of Classification Search
CPC ......... G06T 7/97; G06T 15/00; G06T 15/005; G06T 15/08; G06T 17/00; G06T 17/005; G06T 2200/00; G06T 2200/04; G06T 2200/08; G06T 2200/28; G06T 2200/2207; G06T 2200/10072; G06T 2200/10076; G06T 2200/10081; G06T 2200/30048; G06T 2200/30101; G06T 2200/30104; A61B 6/00; A61B 6/02; A61B 6/03; A61B 6/46; A61B 6/461; A61B 6/466; A61B 6/48; A61B 6/481; A61B 6/486; A61B 6/50; A61B 6/503; A61B 6/504; A61B 6/507; A61B 6/52; A61B 6/5211; A61B 6/5217; A61B 6/5288; A61B 6/5294; A61B 2576/00; A61B 2576/02; A61B 2576/023; G16H 30/00; G16H 30/40; G01N 23/046; G01N 2223/305; G01N 2223/306; G01N 2223/40; G01N 2223/401; G01N 2223/404; G01N 2223/405; G01N 2223/419; G01N 2223/42; G01N 2223/425

See application file for complete search history.

(56) References Cited

U.S. PATENT DOCUMENTS

| | | |
|---|---|---|
| 10,258,303 B2 | 4/2019 | Grass |
| 2012/0243761 A1 | 9/2012 | Senzig |
| 2014/0303495 A1* | 10/2014 | Fonte .................... A61B 6/507 600/425 |
| 2016/0378947 A1* | 12/2016 | Taylor .................... G16H 30/40 705/2 |
| 2018/0315184 A1 | 11/2018 | Freiman |
| 2019/0209115 A1 | 7/2019 | Freiman |

FOREIGN PATENT DOCUMENTS

| | | |
|---|---|---|
| WO | WO2015032647 A1 | 3/2015 |
| WO | WO2015092588 A2 | 6/2015 |
| WO | WO2016145010 A1 | 9/2016 |
| WO | WO2016161308 A1 | 10/2016 |

OTHER PUBLICATIONS

Finegold J. A. et al., "Mortality from Ischaemic Heart Disease by Country, Region, and Age: Statistics from World Health Organisation and United Nations," Int. J. Cardiol., vol. 168, No. 2, pp. 934-945, 2013.

Nowbar A. N. Nowbar et al., "2014 Global Geographic Analysis of Mortality from Ischaemic Heart Disease by Country, Age and Income: Statistics from World Health Organisation and United Nations," Int. J. Cardiol., vol. 174, No. 2, pp. 293-298, 2014.

Heo R. et al. "Noninvasive Imaging in Coronary Artery Disease," Seminars in Nuclear Medicine, vol. 44, No. 5. pp. 398-409, 2014.

Vargas-Szemes A. et al., "CT Myocardial Perfusion Imaging," AJR. Am. J. Roentgenol., vol. 204, No. 3, pp. 487-497, 2015.

Arbab-Zadeh et al., "Quantification of Coronary Arterial Stenoses by Multidetector CT Angiography in Comparison with Conventional Angiography: Methods, Caveats, and Implications," JACC: Cardiovascular Imaging, vol. 4, No. 2. pp. 191-202, 2011.

Meijboom W. B. et al., "Comprehensive Assessment of Coronary Artery Stenoses. Computed Tomography Coronary Angiography Versus Conventional Coronary Angiography and Correlation With Fractional Flow Reserve in Patients With Stable Angina," J. Am. Coll. Cardiol., vol. 52, No. 8, pp. 636-643, 2008.

Coenen A. et al., "Fractional Flow Reserve Computed from Non-invasive CT Angiography Data: Diagnostic Performance of an On-Site Clinician-Operated Computational Fluid Dynamics Algorithm," Radiology, vol. 274, No. 3, pp. 674-683, 2015.

Norgaard B. L. et al., "Diagnostic Performance of Non-Invasive Fractional Flow Reserve Derived from Coronary CT Angiography in Suspected Coronary Artery Disease: The NXT trial.," J. Am. Coll. Cardiol., vol. 63, No. 12, pp. 1145-1155, 2014.

Huo Y. et al., "Intraspecific Scaling Laws of Vascular Trees.," J. R. Soc. Interface, vol. 9, No. 66, pp. 190-200, 2012.

Termeer M. et al., "Visualization of Myocardial Perfusion Derived from Coronary Anatomy," in IEEE Transactions on Visualization and Computer Graphics, 2008, vol. 14, No. 6, pp. 1595-1602.

* cited by examiner

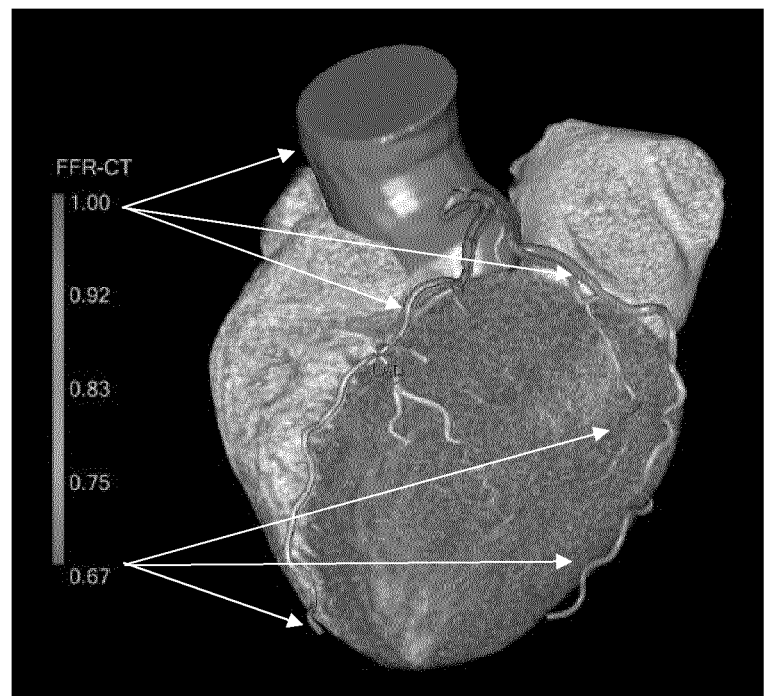
FIG 1 – PRIOR ART
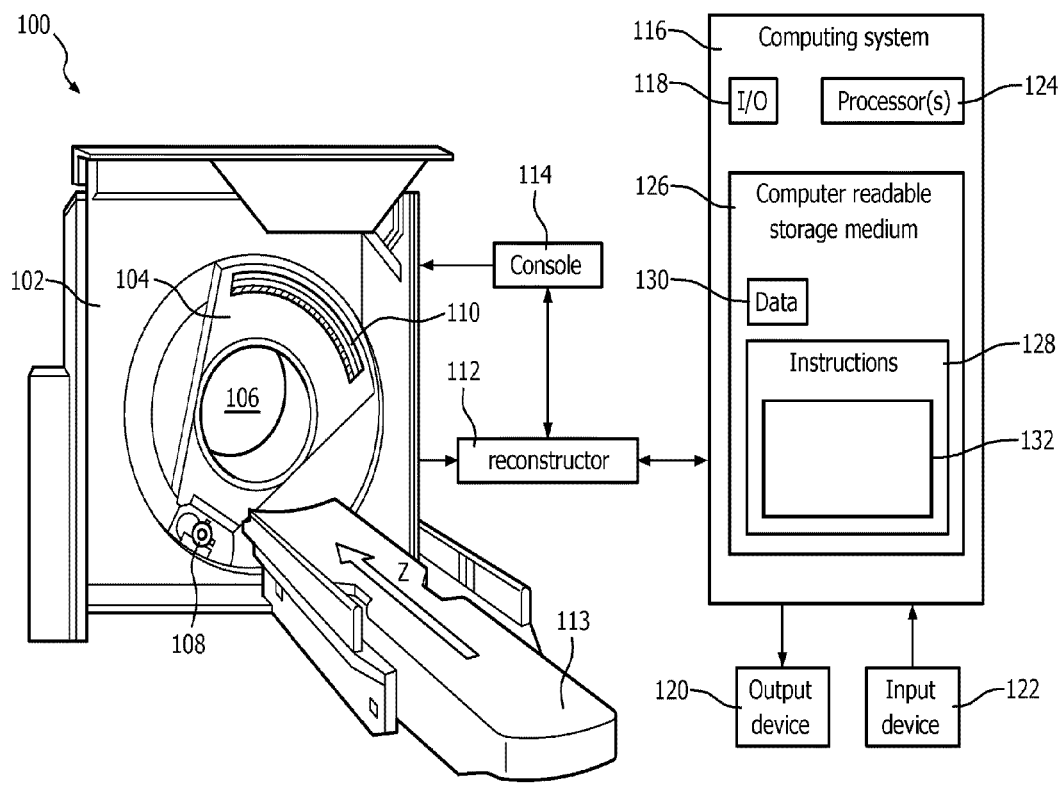
FIG 2

MYOCARDIAL CT PERFUSION IMAGE SYNTHESIS

FIELD OF THE INVENTION

The invention relates to the field of digital image processing. More specifically it relates to myocardial computed tomography (CT) perfusion image synthesis based on spectral CT data, e.g. coronary CT angiography data.

BACKGROUND OF THE INVENTION

Coronary artery disease (CAD) is an important cause of death worldwide. In coronary artery disease, accumulation of plaque material in the coronary arteries limits the supply of oxygen to the cardiac muscle, resulting in myocardial ischemia.

Non-invasive imaging techniques known in the art for assessing the cardiac muscle viability include Myocardial Perfusion Imaging (MPI), in which nuclear imaging modalities such as SPECT and PET are used, and Cardiac Magnetic Resonance Imaging (CMR). However, it may be a disadvantage of such prior-art approaches that these imaging technologies may be less suitable for enabling a combined detailed anatomic assessment of the coronary arteries and a functional evaluation of the downstream myocardial territory.

In computed tomography (CT), images that reveal the internal structure of an object under study can be obtained by means of penetrating ionizing radiation. Such images, e.g. three-dimensional volumetric image data, can be obtained by applying reconstruction techniques, as known in the art, to projection images obtained by a detector and corresponding to different orientations of a source of penetrating ionizing radiation and the detector with respect to the object, e.g. corresponding to different directions of projecting radiation through the object. The reconstructed image data may be organized in voxels, representative of different positions in the object with respect to a three-dimensional coordinate system, and each voxel may have a value associated therewith, e.g. a greyscale value such as a value expressed in Hounsfield units, that is indicative of attenuation characteristics of the scanned object at the position corresponding to the voxel, e.g. indicative of a radiodensity, e.g. of a relative radiodensity.

Using Coronary Computed Tomography Angiography (CCTA), as known in the art, a non-invasive evaluation of coronary artery disease (CAD) can be performed by assessing coronary stenosis. The detailed anatomical information conveyed by CCTA image datasets and a high negative predictive value in coronary artery disease detection advantageously allow coronary artery disease to be ruled out in symptomatic patients with low to intermediate pre-test probability of disease. However, coronary stenosis, detected by assessment of CCTA data, is an indirect measure of myocardial ischemia. Therefore, CCTA methods known in the art may disadvantageously be limited in enabling a detailed assessment of hemodynamic significance of coronary lesions.

FFR-CT is a method known in the art that allows an assessment of hemodynamic significance of coronary lesions based on CCTA data by evaluating the Fractional Flow Reserve (FFR), which refers to the ratio between the pressure distal to the lesion and the pressure before the lesion. FFR-CT therefore can potentially improve the specificity of CCTA in determining hemodynamically significant coronary disease. This approach uses numerical flow simulation based on the CCTA data to infer the FFR metric. For such flow simulation, a three-dimensional tree model of the coronaries and an accurate boundary conditions model for modelling the interface with the non-imaged vasculature may be needed. Therefore, an accurate segmentation of the coronaries, based on the CCTA image data, may be required to build an accurate flow simulation model for FFR-CT.

In FFR-CT, a hemodynamic significance of a lesion can be reported by local FFR-CT values at the lesion, e.g. in a region of a vessel where stenosis is observed, or in the form of a three-dimensional mesh model of the coronary artery tree that is color-coded to represent the FFR-CT values, e.g. as illustrated in FIG. 1. Therefore, the user is limited to an assessment of the coronary lesion, rather than being provided with a means for directly assessing the viability of the cardiac muscle.

It is also known in the art to present flow simulation results obtained from CCTA analyze using a "Bull's-eye" view, e.g. like such views in cardiac nuclear imaging. However, it is a disadvantage that such views may be limited to a two-dimensional representation of the left ventricle, rather than allowing a three-dimensional assessment of perfusion over the entire CT volume.

Dynamic myocardial CT perfusion is another known technique based on CT image data that allows to characterize the viability of the cardiac muscle directly. CT assessment of myocardial perfusion can be either static or dynamic. Furthermore, data may be acquired in a rest and/or stress state. The user can visually assess the perfusion CT images, or may use a software to generate quantitative perfusion maps for more objective evaluation. While cardiac muscle viability can be visualized and assessed directly by such approach, it is a disadvantage of performing at least one additional CT perfusion scan that this implies an additional exposure of the patient to ionized radiation and a toxic contrast agent, e.g. in addition to the radiation exposure and the amount of contrast agent used for performing a CCTA scan. Furthermore, between a CCTA scan and a CT perfusion scan, a time delay may be required to sufficiently reduce the residual contrast agent used for the CCTA scan in the body, which may limit the implementation in clinical practice. It may be another disadvantage that the quantitative maps derived from physically acquired data may be noisy and unreliable due to a limited number of time points, e.g. caused by physical limitations of the data acquisition and/or in view of radiation dose management, compared to the complexity of the perfusion models used to generate the maps.

WO 2015/092588 discloses a method for use in coronary dual-energy CT. The method comprises obtaining contrast enhanced spectral image data of tubular structures, generating a contrast map based on the obtained contrast enhanced spectral image data and generating an updated contrast map based on a spectral model. The method further includes segmenting the tubular structure based on the updated contrast map.

SUMMARY OF THE INVENTION

It is an object of embodiments of the present invention to provide a good and efficient analysis, image synthesis and/or visualization of myocardial function and/or myocardial anatomical structure using computed tomography technology.

The above objective is accomplished by a method and device in accordance with the present invention.

It is an advantage of embodiments of the present invention that a detailed assessment of coronary lesions can be enabled using computed tomography data.

It is an advantage of embodiments of the present invention that a good functional assessment in myocardial CT can be enabled, e.g. allowing a hemodynamic significance of coronary lesions to be determined, e.g. allowing a good assessment of a myocardial ischemia condition.

It is an advantage of embodiments of the present invention that a user can perform a direct functional assessment of coronary lesions, e.g. of myocardial viability, using analyzed CT data.

It is an advantage of embodiments of the present invention that a good assessment of coronary lesions in a subject can be achieved using CT technology at an acceptable, e.g. a low, radiation exposure of the subject.

It is an advantage of embodiments of the present invention that an amount of contrast agent to obtain a good assessment of coronary lesions in a subject can be limited, e.g. advantageously low.

It is an advantage of embodiments of the present invention that a good assessment of coronary lesions in a subject can be achieved in a quick and efficient scanning procedure.

It is an advantage of embodiments of the present invention that a low-noise, accurate, robust and/or reliable quantitative map of perfusion can be provided.

In a first aspect, embodiments of the present invention relate to an image processing device comprising a data input for receiving spectral computed tomography volumetric image data organized in voxels, wherein the volumetric image data comprises a contrast-enhanced volumetric image of a cardiac region in a subject's body and a baseline volumetric image of that cardiac region, e.g. a volumetric image representative for the baseline anatomy of the cardiac region of the subject. The baseline volumetric image conveys baseline anatomical information of the subject, e.g. in which the image contrast of the vasculature with respect to its local neighborhood, e.g. with respect to surrounding tissue, is not significantly different from a case where the subject would be imaged in the absence of an intravenous contrast agent, e.g. even where the raw data on which the baseline volumetric image is based was acquired in the presence of such agent in the vasculature, such as for example by using a virtual non-contrast-enhanced volumetric image based on a scan of the subject having an intravenous contrast agent introduced into the blood flow.

The contrast-enhanced volumetric image conveys anatomical information regarding coronary artery anatomy of the subject, e.g. specific anatomical information regarding the coronary artery anatomy that is not present, e.g. discernably present, in the baseline volumetric image. The image processing device comprises a flow simulator for generating, or receiving as input, a three-dimensional coronary tree model based on the volumetric image data and for simulating a coronary flow based on the three-dimensional coronary tree model. The image processing device comprises a perfusion synthesis unit for generating a perfusion image representative of a blood distribution in tissue at at least one instant in time taking at least the baseline volumetric image and the coronary flow simulation into account. For example, an instant in time may refer to a point in time, or may refer to a predetermined time interval, e.g. a short time interval, e.g. a time interval having a predetermined length in time, such as a length in time in the range of 0 ms to 2 s, e.g. in the range of 10 ms to 1 s, e.g. in the range of 50 ms to 500 ms.

In an image processing device in accordance with embodiments of the present invention, the data input may be adapted for receiving the volumetric image data comprising the baseline volumetric image, in which the baseline volumetric image has the form of a virtual non-contrast-enhanced volumetric image of the cardiac region, and in which the contrast-enhanced volumetric image and the virtual non-contrast-enhanced volumetric image are based on a same spectral cardiac CT dataset obtained in a single spectral CT acquisition sequence. For example, the virtual non-contrast-enhanced volumetric image may refer to a volumetric image obtained by manipulation of the spectral cardiac CT dataset such that an influence on the image contrast of an intravenous contrast agent present in the imaged region is reduced or, preferably substantially removed, e.g. as obtainable by a method for virtual non-contrast (VNC) image construction that is known in the art.

In an image processing device in accordance with embodiments of the present invention, the flow simulator may comprise a coronary tree segmentation unit for generating the three-dimensional coronary tree model based on the volumetric image data.

In an image processing device in accordance with embodiments of the present invention, the flow simulator may be adapted for simulating the coronary flow by taking a boundary condition model for modelling an interface between the three-dimensional coronary tree model and non-imaged connecting vasculature, e.g. non-imaged vasculature in a local neighborhood of and/or adjacent to the imaged coronary tree, into account.

In an image processing device in accordance with embodiments of the present invention, the flow simulator may comprise a boundary condition processor for determining the boundary condition model taking a fluidodynamic resistance of the non-imaged vasculature that is based on a cross-section area of each coronary outlet into account.

In an image processing device in accordance with embodiments of the present invention, the perfusion synthesis unit may be adapted for determining a myocardium feeding territory in the volumetric image data for each coronary, e.g. each segment, in the three-dimensional coronary tree model. For example, a myocardium feeding territory may refer to a region of the myocardium that is assigned to a corresponding part of the coronary tree model, e.g. to a specific coronary artery branch, from which part of the coronary tree model the myocardial region is predominantly supplied of nutrients and/or oxygen. Or, in other words, the myocardium feeding territory may refer to that region of the myocardium that is fed, or at least assumed to be mainly fed, by the part of the coronary tree that is corresponds to.

In an image processing device in accordance with embodiments of the present invention, the perfusion synthesis unit may be adapted for determining the myocardium feeding territory for each coronary by calculating a Voronoi diagram and/or Delaunay triangulation relating the volumetric image data to the coronary tree model. However, embodiments of the invention are not necessarily limited to such methods for calculating the myocardium feeding territory, and may additionally or alternatively implement other methods as known in the art for flow territory mapping, e.g. of a vascular system.

In an image processing device in accordance with embodiments of the present invention, the perfusion synthesis unit may be adapted for determining the myocardium feeding territory for each coronary by registering a generic feeding model to the specific subject using the coronary tree model and/or the volumetric image data.

In an image processing device in accordance with embodiments of the present invention, the perfusion synthesis unit may be adapted for calculating an amount of contrast agent in at least one voxel of the myocardium at the at least one instant in time based on a flow, in accordance with the coronary flow simulation, e.g. as obtained from the coronary flow simulation, in a coronary that corresponds to the myocardium feeding territory to which the at least one voxel is attributed, and based on a blood diffusion model.

In an image processing device in accordance with embodiments of the present invention, the perfusion synthesis unit may be adapted for calculating, for the (or each) at least one voxel and the (or each) at least one instant in time, an image voxel value by adding a voxel value indicative of the amount of contrast agent in the at least one voxel at the at least one instant in time to an image voxel value of the baseline volumetric image.

In an image processing device in accordance with embodiments of the present invention, the perfusion synthesis unit may be adapted for synthesizing the perfusion image by iteratively minimizing a combination of an image distance measure between the perfusion image and an image comprising the at least one calculated voxel and a regularization term representative of an image quality measure of the perfusion image.

In a second aspect, embodiments of the present invention also relate to a computed tomography workstation comprising an image processing device in accordance with embodiments of the first aspect of the present invention.

In a third aspect, embodiments of the present invention also relate to a spectral computed tomography system comprising an image processing device in accordance with embodiments of the first aspect of the present invention.

In a fourth aspect, embodiments of the present invention relate to a method for volumetric image processing. The method comprises receiving spectral computed tomography volumetric image data organized in voxels, in which the volumetric image data comprises a contrast-enhanced volumetric image of a cardiac region in a subject's body and a baseline volumetric image of the cardiac region. The contrast-enhanced volumetric image conveys anatomical information regarding coronary artery anatomy of the subject. The method comprises generating, or receiving as input, a three-dimensional coronary tree model based on the volumetric image data. The method comprises simulating a coronary flow based on the three-dimensional coronary tree model. The method comprises generating a perfusion image representative of a blood distribution in tissue at at least one instant in time taking at least the baseline volumetric image and the coronary flow simulation into account.

In a yet further aspect, embodiments of the present invention also relate to a computer readable storage medium encoded with one or more computer executable instructions, which, when executed by a processor of a computing system, causes the computing system to perform a method in accordance with embodiments of the present invention.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 1 shows an exemplary visualization obtainable by a Fractional Flow Reserve computed tomography (FFR-CT) simulation as known in the art. In such prior-art visualization, the FFR information may be presented by a color-coded overlay of the vessels on a greyscale anatomical background image, as indicated by the color gradient bar and the arrow pointers.

FIG. 2 schematically illustrates an imaging system comprising an image processing device in accordance with embodiments of the present invention.

Figure 3:
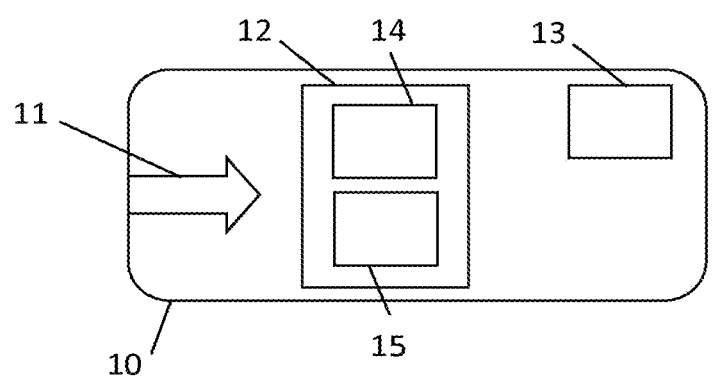
FIG. 3 schematically illustrates an image processing device in accordance with embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, embodiments of the present invention relate to an image processing device that comprises a data input for receiving spectral computed tomography volumetric image data organized in voxels. This volumetric image data comprises a contrast-enhanced volumetric image of a cardiac region in a subject's body and a baseline volumetric image of that cardiac region. The contrast-enhanced volumetric image conveys anatomical information regarding coronary artery anatomy of the subject, e.g. anatomical information that is not conveyed by the baseline volumetric image, e.g. anatomical information that is contrast-enhanced due to use of an intravenous radiocontrast agent, such as an iodine-based contrast medium for intravascular use. The image processing device also comprises a flow simulator for generating or receiving, as input, a three-dimensional coronary tree model based on the volumetric image data and for simulating a coronary flow simulation based on the three-dimensional coronary tree model. The image processing device furthermore comprises a perfusion synthesis unit for generating at least one perfusion image, e.g. at least one virtual perfusion image, representative of a blood distribution in tissue, at at least one instant in time, taking at least the baseline volumetric image and the coronary flow simulation into account.

FIG. 3 illustrates an exemplary image processing device 10 in accordance with embodiments of the present invention. The image processing device may comprise a computing device, such as a computer programmed for providing the functionality as described hereinbelow. The computing device may comprise a configurable hardware device, e.g. a field-programmable gate array, configured for providing the intended functionality or may comprise application specific circuitry specifically designed for providing the intended functionality. The computing device may comprise any combination of designed hardware, configured hardware and/or software for executing on general purpose hardware.

Thus, components of an image processing device 10 in accordance with embodiments of the present invention, such as a data input 11, a flow simulator 12 and/or a perfusion synthesis unit 13, do not necessarily correspond to physically separate entities of such device, e.g. physically separable components, but may refer to a software construct that is implemented in a computer code for executing on a general purpose computer.

The image processing device 10 comprises a data input 11 for receiving spectral computed tomography (CT) volumetric image data organized in voxels. Particularly, the data input may comprise a digital communication circuit, such as a computer network interface, a wireless transmission interface or a digital data bus interface, for receiving the data from an external source, such as a spectral CT scanner or a reconstructor for reconstructing CT images provided by a spectral CT scanner. The data input may comprise a virtual interface for receiving the data from another software component implemented on a shared hardware platform, e.g. from another software component executing on the same computer, such as a software component for reconstructing spectral CT image data. Such virtual interface may for example comprise an application programming interface, a shared memory resource or a file stored using a filesystem standard on a data carrier. The data input may comprise an interface for accessing a data carrier, such as an optical disk reader, a universal serial bus (USB) connection for accessing a USB data storage medium, a magnetic disk reader or a portable flash drive reader. The data input may comprise any combination of the means mentioned hereinabove, and/or other devices known in the art suitable for receiving digital volumetric image data.

The spectral CT volumetric image data is organized in voxels, e.g. comprising a plurality of data values linked to corresponding voxel locations in a scanned object, e.g. a scanned subject. The spectral CT volumetric image data may thus comprise reconstructed image data organized in voxels, e.g. representative of different positions in the scanned object with respect to a three-dimensional coordinate system. The spectral CT volumetric image data may also comprise volumetric image data derived, e.g. calculated from, such reconstructed image data organized in voxels.

Each voxel may have a value associated therewith, e.g. a greyscale value such as a value expressed in Hounsfield units, that is indicative of attenuation characteristics of the scanned object at the position corresponding to the voxel, e.g. indicative of a radiodensity, e.g. of a relative radiodensity. The volumetric image data may comprise at least two different greyscale values associated with the same voxel location, e.g. for each voxel location in the cardiac region. Each of the at least two different greyscale values may thus be indicative of different attenuation characteristics at the corresponding voxel location, e.g. for different qualities of penetrating ionizing radiation. The different qualities of penetrating ionizing radiation may differ sufficiently in mean and/or peak photon energy such that the different attenuation characteristics may be subject to discernibly different photoelectric effect and Compton effect contributions, e.g. indicative of different tissues and/or tissue properties in the subject. However, the different greyscale values need not correspond to, or be limited to, attenuation characteristics directly related to qualities of penetrating ionizing radiation the subject was exposed to in order to acquire the image data. For example, at least one of the different greyscale values (e.g. for each voxel) may be representative for an abstracted material property that was not directly observed, but inferred by combining and/or manipulating the directly acquired or reconstructed images. For example different scalar values per voxel may, in some embodiments, correspond to an arbitrary basis decomposition, as opposed to corresponding to physical energy spectra of ionizing radiation and/or detector characteristics used in scanning the object. For example, such scalar values may form an 80 kVp and/or a 120 kVp component image, a water-material, a bone-material and/or an iodine image and/or a monochromatic virtual image.

The spectral CT volumetric image data may for example comprise, or be derivable from, Dual-Energy (DE) CT volumetric image data or spectral CT volumetric image data based on more than two different imaged radiation qualities. The image data may be acquired, e.g. pre-recorded, using a spectral CT scanning technique known in the art, e.g. a dual energy scan approach as known in the art, such as acquisition using a scanner having a dual-source or multi-source configuration, a scanner adapted for fast kVp switching while scanning and/or a scanner having a dual-layer or multi-layer detector configuration.

The spectral CT volumetric image data may for example comprise, or consist of, computed tomography cardiac angiography data, e.g. in accordance with a standard spectral CT acquisition protocol as known in the art for cardiac angiography.

The volumetric image data comprises a contrast-enhanced volumetric image of a cardiac region in a subject's body and a baseline volumetric image of that cardiac region. The contrast-enhanced volumetric image conveys anatomical information regarding coronary artery anatomy of the subject, e.g. additional information that is not conveyed by the baseline volumetric image.

For example, the volumetric image data may comprise combined and/or monoenergetic images as the contrast-enhanced volumetric image and/or the baseline volumetric image. For example, the volumetric image data may comprise an iodine map, e.g.

a volumetric image calculated from the spectral CT data such that voxel values in the image are indicative of an amount of iodine present at corresponding voxel locations in the imaged region.

In accordance with embodiments of the present invention, the data input 11 may be adapted for receiving the volumetric image data comprising the baseline volumetric image in the form of a virtual non-contrast-enhanced volumetric image of the cardiac region. Thus, the contrast-enhanced volumetric image and the virtual non-contrast-enhanced volumetric image may be based on a same spectral cardiac CT dataset obtained in a single spectral CT volumetric acquisition. It is an advantage of spectral CT that a single volumetric acquisition can be used, or processed, to present both an image that shows little or no contribution of the presence of a contrast agent in the imaged region and an image that strongly enhances and/or isolates such contribution of the presence of the contrast agent. For example, repetitive scanning, which might imply a higher radiation dose to the subject, may be advantageously reduced or avoided and registration and/or misalignment artefacts may be reduced or avoided. It is an advantage of spectral CT that iodine can be distinguished from other materials having similar attenuation characteristics, e.g. from calcium. Thus vessel surface structures can be more easily detected, e.g. particularly where such surface structures are adjacent to, for example, a bone material.

For example, the contrast-enhanced volumetric image, e.g. showing an anatomical background with highlighted coronary artery anatomy or alternatively showing substantially only the coronary artery anatomy without anatomical background information of the surrounding tissue, may be used for coronary segmentation and flow simulation and the baseline volumetric image, e.g. the virtual non-contrast-enhanced volumetric image, may be used as baseline reference for perfusion synthesis in accordance with embodiments of the present invention.

The image processing device 10 also comprises a flow simulator 12 for generating or receiving, as input, a three-dimensional coronary tree model based on the volumetric image data and for simulating a coronary flow, e.g. generating a coronary flow simulation, based on the three-dimensional coronary tree model, e.g. by taking the contrast-enhanced volumetric image into account, e.g. based on the contrast-enhanced volumetric image.

For example, the coronary tree model may be obtained as input from a Cardiac CT reading workstation having capabilities for generating such model, as known in the art. For example, the coronary tree model may be obtained as input from the Comprehensive Cardiac Application commercially available at the Philips Intellispace Portal equipped with centerline extraction and coronary lumen segmentation algorithms and/or interactive segmentation and/or tree modelling tools.

The flow simulator 12 may comprise a coronary tree segmentation unit 14 for generating the three-dimensional coronary tree model based on the volumetric image data, e.g. by taking the contrast-enhanced volumetric image into account, e.g. based on the contrast-enhanced volumetric image. The segmentation unit may for example be adapted for coronary lumen segmentation, for extracting a vessel centerline and/or building a tree model from such branching centerline structures.

The flow simulator 12 may be adapted for simulating the coronary flow by taking a boundary condition model into account. This boundary condition model may model an interface between the three-dimensional coronary tree model and non-imaged vasculature.

The flow simulator 12 may comprise a boundary condition processor 15 for determining the boundary condition model, taking a fluidodynamic resistance of the non-imaged vasculature into account, in which this fluidodynamic resistance may be based on a cross-section area of each coronary outlet.

For example, the boundary condition model may be adapted for distributing an overall resistance of the non-imaged vasculature among the different coronary outlets based on their cross section area. For example, the overall resistance can be distributed in accordance with a relation between flows in the vessel and its branches with respect to their diameters. e.g.:

$$R_i = R_0 \cdot \frac{r_{in}^{\frac{1}{3}} \cdot \rho_{blood} \cdot r_{out,i}^{-\frac{7}{3}}}{\pi} \left[ \frac{g}{cm^4 \cdot s} \right]$$

In which $R_i$ refers to a resistance in a vessel, $R_0$ refers to the resistance in a parent of the vessel in the tree structure, $r_{in}$ refers to a radius of the parent, $r_{out,i}$ to a radius of the branch, and $\rho_{blood}$ to the mass density of blood. The diameters and/or cross section areas of the vessels may be determined based on, or by, the coronary tree model.

However, embodiments of the present invention are not limited to this specific choice of resistance model, and may be practiced using any suitable boundary model for coronary flow simulation known in the art.

The flow simulation may be performed in accordance with methods known in the art, e.g. using a 3D computational fluid dynamics (CFD) approach, or a reduced-order approach, e.g. as known in the art for FFR-CT analysis.

The image processing device 10 also comprises a perfusion synthesis unit 13 for generating a perfusion image representative of a blood distribution in tissue, at at least one instant in time, e.g. for generating a time sequence of perfusion images representative for perfusion at different instants in time, taking at least the baseline volumetric image and the coronary flow simulation into account.

The perfusion synthesis unit 13 may be adapted for determining a myocardium feeding territory in the volumetric image data for each coronary in the three-dimensional coronary tree model. For example, each voxel in the baseline volumetric image may be thus assigned to the feeding territory of a single coronary in the 3D coronary tree model.

The perfusion synthesis unit 13 may be adapted for determining the myocardium feeding territory for each coronary by calculating a Voronoi diagram or Delaunay triangulation relating the volumetric image data to the coronary tree model, e.g. by calculating the Voronoi tessellation or Delaunay triangulation of the 3D coronary tree model.

The perfusion synthesis unit 13 may be adapted for determining the myocardium feeding territory for each coronary by registering a generic feeding model to the specific subject using the coronary tree model and/or the volumetric image data. For example, a non-rigid registration of the contrast-enhanced volumetric image to an anatomical reference volumetric image of the coronary system may be performed, or a registration, e.g. a line segment-based or a mesh-based registration, of the coronary tree model to an anatomical reference coronary tree model may be performed.

For example, the 17-segment model of the American Heart Association (AHA) may be registered to a specific patient, e.g. to the coronary tree model obtained for the subject.

However, embodiments of the present invention are not limited to this specific reference model, and may be practiced using any suitable reference model of generic coronary artery anatomy known in the art. Furthermore, embodiments of the present invention are not limited to these specific examples of determining the myocardium feeding territory for each coronary, and may be used in combination with any suitable method known in the art for determining the myocardium feeding territory.

The perfusion synthesis unit 13 may be adapted for calculating an amount of contrast agent in at least one voxel of the myocardium at the at least one instant in time, e.g. for a plurality of time points in a sequence. This calculation may be based on a flow, in accordance with the coronary flow simulation, in a coronary that corresponds to the myocardium feeding territory to which the at least one voxel is attributed, e.g. assigned, and based on a blood diffusion model.

For example, one such model is disclosed in Yipintsoi et al., "Nonlinear model for capillary-tissue oxygen transport and metabolism," Ann. Biomed. Eng. 25(4), pp. 604-619, 1997. However, embodiments of the present invention are not limited to such exemplary model.

The perfusion synthesis unit 13 may be adapted for calculating the at least one voxel at said at least one instant in time an image voxel value by adding a voxel value indicative of the amount of contrast agent in the (or each of the) at least one voxel at the (or each of the) at least one instant in time to an image voxel value of the baseline volumetric image.

For example, a Hounsfield unit (HU) value for each voxel at each time-point may be calculated by summation of the baseline HU of the tissue obtained from the baseline image, e.g. the virtual non-contrast-enhanced image, with the HU associated with the contrast material arrived in the voxel at the given time point:

$$x(\vec{p},t)=vnc(\vec{p})+\text{per}(\vec{p},t)$$

in which $\vec{p}$ refers to the coordinates of the pixel to estimate the HU value for at time t, vnc refers to the baseline image, e.g. the virtual non-contrast-enhanced image, and per refers to the HU increase in the tissue due to flow in the coronaries propagated in accordance with a perfusion model, e.g. as described hereinabove.

The perfusion synthesis unit 13 may be adapted for synthesizing the perfusion image by iteratively minimizing a combination, e.g. a sum, of an image distance measure between the perfusion image, e.g. a current perfusion image in a sequence of perfusion images corresponding to a sequence of iterations in the optimization process, and an image comprising the (or each of the) at least one calculated voxel and a regularization term representative of an image quality measure of the perfusion image, such as a measure indicative of smoothness, uniformity, edge sharpness and/or other image quality measures as known in the art.

For example, the regularization constraint may be used in a total variation minimization optimizer to obtain a smooth image, e.g. in accordance with:

$$E(y(t)) = \min_y E(x(t), y(t)) + \lambda TV(y(t))$$

where y(t) is the synthesized perfusion image at time point t, x(t) is the model estimated perfusion image, such as obtainable by applying the formula for x(t) hereinabove to the entire volume, TV is the regularization term, and λ is a weighting parameter that controls the amount of regularization to be applied.

Furthermore, additional perfusion-related information from the spectral images may be incorporated into such regularized minimization. For example, an iodine map can be used to enhance perfusion deficit regions.

The device may also comprise a perfusion map generator for computing quantitative perfusion maps from a sequence, e.g. a time series, of perfusion images generated by the perfusion synthesis unit 13. Such perfusion map generator may apply a method for calculating a quantitative perfusion map based on conventional dynamic cardiac perfusion CT images as known in the art, e.g. a prior-art method for processing physically acquired dynamic cardiac perfusion CT images. However, in embodiments of the present invention, such time series may be accurately simulated without requiring the physical acquisition of a series of dynamic cardiac perfusion CT images, which therefore can be advantageous for limiting the radiation exposure of the subject, for time efficiency and for obtaining a high temporal resolution of the perfusion time series, e.g. for simulating a large number of time points, which may improve the numerical stability and accuracy when calculating a quantitative perfusion map.

In a second aspect, embodiments of the present invention also relate to a computed tomography workstation comprising an image processing device in accordance with embodiments of the first aspect of the present invention.

In a third aspect, embodiments of the present invention also relate to a spectral computed tomography system comprising an image processing device in accordance with embodiments of the first aspect of the present invention. For example, embodiments of the present invention may relate to a spectral computed tomography system such as the imaging system 100 described hereinbelow in relation to FIG. 2.

FIG. 2 illustrates an imaging system 100 comprising a spectral computed tomography (Spectral CT) scanner. The imaging system 100 may comprise a generally stationary gantry 102 and a rotating gantry 104. The rotating gantry 104 may be rotatably supported by the stationary gantry 102 and may rotate around an examination region 106 about a longitudinal axis Z.

A radiation source 108, such as an x-ray tube, may be rotatably supported by the rotating gantry 104, e.g. such as to rotate with this rotating gantry 104, and may be adapted for emitting poly-energetic radiation that traverses the examination region 106. The radiation source 108 may comprise, or consist of, a single broad spectrum x-ray tube. Alternatively, the radiation source may be adapted for controllably switching between at least two different photon emission spectra, e.g. switching between at least two different peak emission voltages, such as 80 kVp, 140 kVp, etc., during scanning. In another variation, the radiation source 108 may comprise two or more x-ray tubes configured to emit radiation with different mean spectrums. In another variation, the radiation source 108 may comprise a combination of the above.

A radiation sensitive detector array 110 may subtend an angular arc opposite the radiation source 108 across the examination region 106. The array 110 may include one or more rows of detectors arranged with respect to each other along the Z-axis direction. The array 110 may be adapted for detecting radiation traversing the examination region 106, and generating signals indicative thereof. The array 110 may comprise a dual-energy detector with at least two radiation sensitive detector elements having different x-ray energy sensitivities, e.g. at least two scintillators and at least two corresponding photosensors having corresponding optical sensitivities. The radiation sensitive detector array 110 may alternatively or additionally comprise a direct conversion detector, such as a CdTe, CdZnTe or other direct conversion detector known in the art.

The system may comprise a reconstructor 112 for reconstructing the signals output by the detector array 110. This may include decomposing the signal into various energy dependent components. The reconstructor 112 may be adapted for reconstructing the energy dependent components and generating one or more images corresponding to one or more different energies. The reconstructor 112 may also combine the energy dependent components to generate non-spectral image data.

The system may comprise a subject support 113, such as a couch, for supporting an object or subject in the examination region. The system may also comprise an operator console 114, e.g. a general purpose computer programmed for controlling or monitoring the system 100 and/or for providing a user interface for an operator. The console 114 may include a human readable output device such as a monitor or display and an input device such as a keyboard and mouse. Software resident on the console 114 may allow the operator to interact with the scanner 100 via a graphical user interface (GUI) or otherwise. This interaction may include selecting a spectral imaging protocol or a non-spectral imaging protocol, initiating scanning, etc.

The imaging system 100 may be operably connected to a workstation, e.g. computing system 116, such as a computer, that may comprise an input/output (I/O) interface 118 for facilitating communication with the spectral CT scanner. The imaging system 100 may comprise the computing system 116 as a system-level integrated component, or the imaging system 100 may be adapted for communicating with a stand-alone computing system 116, e.g. to transmit image data to the computing system 116.

The computing system 116 may further comprise an output device 120. The output device or output devices may comprise, for example, a display monitor, a film printer, a paper printer and/or an audio output for audio feedback. The computing system may also comprise an input device 122 or input devices, such as a mouse, a keyboard, a touch interface and/or a voice recognition interface. The computing system 116 may also comprise at least one processor 124, such as a central processing unit (CPU), a microprocessor, a dedicated application-specific integrated circuit (ASIC) for processing and/or an appropriately configured programmable hardware processor such as a field-programmable gate array. The computing system may comprise a computer readable storage medium 126, e.g. a non-transitory memory such as a physical digital memory. The computer readable storage medium 126 may store computer readable instructions 128 and data 130. The at least one processor 124 may be adapted for executing the computer readable instructions 128. The at least one processor 126 may also execute computer readable instructions carried by a signal, carrier wave or other transitory medium. Alternatively or additionally, the at least one processor may be physically configured to embody the instructions 128, e.g. entirely or in part, without necessarily requiring memory storage of these instructions, e.g. by configuration of a field-programmable gate array or an ASIC specifically designed to carry out at least a part of the instructions.

The computing system may be programmed, e.g. in accordance with the computer readable instructions referred to hereinabove, to implement an image processing device 10 in accordance with embodiments of the first aspect of the present invention.

The instructions 128 may comprise an image processing algorithm 132 for performing a method in accordance with embodiments of a fourth aspect of the present invention.

In a further aspect, embodiments of the present invention also relate to a method for volumetric image processing, e.g. for spectral CT volumetric image processing.

The method comprises receiving spectral computed tomography volumetric image data organized in voxels. The volumetric image data comprises a contrast-enhanced volumetric image of a cardiac region in a subject's body and a baseline volumetric image of that cardiac region, wherein the contrast-enhanced volumetric image conveys anatomical information regarding coronary artery anatomy of the subject, e.g. additional anatomical information regarding the coronary artery anatomy not conveyed by the baseline volumetric image. The method comprises generating, or receiving as input, a three-dimensional coronary tree model based on the volumetric image data. The method comprises simulating a coronary flow based on the three-dimensional coronary tree model. The method comprises generating a perfusion image representative of a blood distribution in tissue at at least one instant in time taking at least the baseline volumetric image and the coronary flow simulation into account.

Details of methods in accordance with embodiments of the present invention shall be clear in relation to the description provided hereinabove relating to embodiments of the first aspect of the present invention. Particularly, functions performed by the data input, the flow simulator and/or the perfusion synthesis unit of a device in accordance with embodiments of the present invention shall be understood as constituting corresponding steps and/or features of a method in accordance with embodiments of the present invention.

Figure 4:
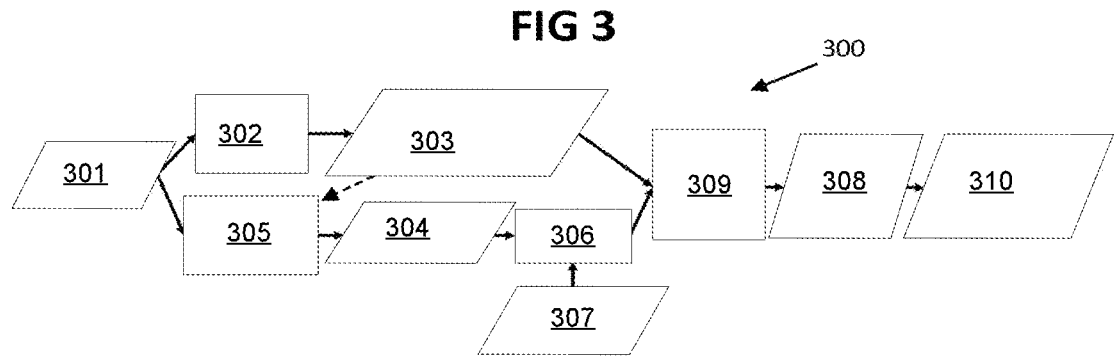
FIG. 4 schematically illustrates a method in accordance with embodiments of the present invention.

FIG. 4 illustrates an exemplary method 300 in accordance with embodiments of the present invention.

The method 300 comprises receiving 301, e.g. obtaining, spectral computed tomography volumetric image data organized in voxels.

The method 300 comprises a step of obtaining 301 spectral computed tomography volumetric image data organized in voxels, e.g. computed tomography angiography data obtained from a spectral CT system or data processor, e.g. spectral coronary CT angiography (CCTA) data. For example, this step may comprise a spectral acquisition and a tomographic reconstruction, e.g. as known in the art and/or explained in more detail in relation to the imaging system shown in FIG. 2.

The volumetric image data comprises a contrast-enhanced volumetric image of a cardiac region in a subject's body and a baseline volumetric image of that cardiac region, wherein the contrast-enhanced volumetric image conveys anatomical information regarding coronary artery anatomy of the subject.

For example, the obtaining 301 the spectral CT volumetric image data may comprise applying spectral processing techniques 302 as known in the art, to provide 303 the contrast-enhanced volumetric image and the baseline volumetric image, e.g. a virtual non-contrast-enhanced volumetric image and an iodine volumetric image. Alternatively, contrast-enhanced volumetric image and the non-contrast-enhanced baseline volumetric image may be obtained 301 directly from an external source.

The method comprises generating 304, or receiving as input, a three-dimensional coronary tree model based on the volumetric image data. For example, the method may comprise segmenting 305, e.g. using a numerical segmentation, a guided manual segmentation executed via a user interface or a hybrid numerical/manual segmentation, the coronary arteries based on the spectral computed tomography volumetric image data, e.g. on a volumetric spectral image having sufficient artery-specific contrast, such as the contrast-enhanced volumetric image.

The method comprises simulating 306 a coronary (fluidic) flow based on the three-dimensional coronary tree model.

The method may also comprise determining 307 a boundary condition model, and using this boundary condition model in the coronary flow simulation 306.

The method comprises generating 308 a perfusion image, e.g. a timeseries of perfusion images, e.g. a virtual dynamic CTP image or timeseries thereof. This perfusion image is representative of a blood distribution in tissue at at least one instant in time taking at least the baseline volumetric image and the coronary flow simulation into account.

For example, the method may comprise using 309 a dynamic perfusion synthesis model representative of perfusion of a contrast agent in the coronary arteries and/or of blood diffusion into tissue supplied via a blood flow in the coronary arteries.

The method may further comprise a step of generating 310 quantitative perfusion maps and/or automated or guided analysis of the perfusion, e.g. providing a summary of quantities relating to the perfusion in a region of interest. For example, since a large number of time points in a temporal sequence can be used for generating 308 a time series of perfusion images, results obtained from quantitative perfusion analysis, e.g. a quantitative perfusion map, may advantageously have a low noise level and/or may be substantially free from imaging artefacts. Thus, high quality quantitative maps may be obtained for further clinical analysis.

In a yet further aspect, embodiments of the present invention also relate to a computer readable storage medium encoded with one or more computer executable instructions, which, when executed by a processor of a computing system, causes the computing system to perform a method in accordance with embodiments of the present invention.

The invention claimed is:

1. An image processing device comprising:
 a memory that stores a plurality of instructions; and
 processor circuitry that couples to the memory and is configured to execute the plurality of instructions to:
  receive spectral computed tomography volumetric image data organized in voxels, said volumetric image data comprising a contrast-enhanced volumetric image of a cardiac region in a subject's body and a baseline volumetric image of said cardiac region, wherein said baseline volumetric image conveys baseline anatomical information of the subject and said contrast-enhanced volumetric image conveys anatomical information regarding coronary artery anatomy of the subject;
  generate or receive as input, a three-dimensional coronary tree model based on said volumetric image data:
  simulate a coronary flow based on said three-dimensional coronary tree model; and
  generate a time sequence of perfusion images representative of a blood distribution in tissue at different instants in time in accordance with the coronary flow simulation, and using the baseline volumetric image as a reference for perfusion synthesis.

2. The image processing device of claim 1, wherein the processor circuitry is further configured to receive said volumetric image data comprising the baseline volumetric image in the form of a virtual non-contrast-enhanced volumetric image of said cardiac region, wherein the contrast-enhanced volumetric image and the virtual non-contrast-enhanced volumetric image are based on a same spectral cardiac CT dataset obtained in a single spectral CT acquisition sequence.

3. The image processing device of claim 1, wherein the processor circuitry is further configured to generate said three-dimensional coronary tree model based on at least said contrast-enhanced volumetric image in said volumetric image data.

4. The image processing device of claim 1, wherein the processor circuitry is further configured to simulate said coronary flow by taking a boundary condition model for modelling an interface between said three-dimensional coronary tree model and non-imaged connecting vasculature into account.

5. The image processing device of claim 4, wherein the processor circuitry is further configured to determine said boundary condition model taking a fluidodynamic resistance of the non-imaged vasculature that is based on a cross-section area of each coronary outlet into account.

6. The image processing device of claim 1, wherein the processor circuitry is further configured to determine a myocardium feeding territory in the volumetric image data for each coronary artery in said three-dimensional coronary tree model.

7. The image processing device of claim 6, wherein the processor circuitry is further configured to determine said myocardium feeding territory for each coronary artery by calculating a Voronoi diagram relating the volumetric image data to the coronary tree model.

8. The image processing device of claim 6, wherein the processor circuitry is further configured to determine said myocardium feeding territory for each coronary artery by registering a generic feeding model to the specific subject using said coronary tree model and/or said volumetric image data.

9. The image processing device of claim 6, wherein the processor, circuitry is further configured to calculate an amount of contrast agent in at least one voxel of the myocardium at said at least one instant in time based on a flow, in accordance with said coronary flow simulation, in a coronary artery that corresponds to the myocardium feeding territory to which said at least one voxel is attributed, and based on a blood diffusion model.

10. The image processing device of claim 9, wherein the processor circuitry is further configured to calculate, for said at least one voxel and said at least one instant in time, an image voxel value by adding a voxel value indicative of the amount of contrast agent in said at least one voxel at said at least one instant in time to an image voxel value of the baseline volumetric image.

11. The image processing device of claim 10, wherein the processor circuitry is further configured to synthesize said perfusion image by iteratively minimizing a combination of an image distance measure between said perfusion image and an image comprising the at least one calculated voxel and a regularization term representative of an image quality measure of said perfusion image.

12. A method for volumetric image processing, the method comprising:
receiving spectral computed tomography volumetric image data organized in voxels, said volumetric image data comprising a contrast-enhanced volumetric image of a cardiac region in a subject's body and a baseline volumetric image of said cardiac region, wherein said contrast-enhanced volumetric image conveys anatomical information regarding coronary artery anatomy of the subject;
generating, or receiving as input, a three-dimensional coronary tree model based on said volumetric image data;
simulating a coronary flow based on said three-dimensional coronary tree model; and
generating a time sequence of perfusion images representative of a blood distribution in tissue at different instants in time in accordance with the coronary flow simulation, and using the baseline volumetric image as reference for perfusion synthesis.

13. A non-transitory computer-readable medium having one or more executable instructions stored thereon, which, when executed by at least one processor, cause the at least one processor to perform a method for volumetric image processing, the method comprising:
receiving spectral computed tomography volumetric image data organized in voxels, said volumetric image data comprising a contrast-enhanced volumetric image of a cardiac region in a subject's body and a baseline volumetric image of said cardiac region, wherein said contrast-enhanced volumetric image conveys anatomical information regarding coronary artery anatomy of the subject;
generating, or receiving as input, a three-dimensional coronary tree model based on said volumetric image data;
simulating a coronary flow based on said three-dimensional coronary tree model; and
generating a time sequence of perfusion images representative of a blood distribution in tissue at different instants in time in accordance with the coronary flow simulation, and using the baseline volumetric image as reference for perfusion synthesis.

14. The image processing device of claim 2, wherein said virtual non-contrast-enhanced volumetric image is based on a scan of the subject having an intravenous contrast agent introduced into the blood flow.

15. The method of claim 12, wherein said receiving comprises receiving said volumetric image data comprising the baseline volumetric image in the form of a virtual non-contrast-enhanced volumetric image of said cardiac region,
wherein the contrast-enhanced volumetric image and the virtual non-contrast-enhanced volumetric image are based on a same spectral cardiac CT dataset obtained in a single spectral CT acquisition sequence, and
wherein said virtual non-contrast-enhanced volumetric image is based on a scan of the subject having an intravenous contrast agent introduced into the blood flow.

* * * * *